United States Patent
Baronov

[11] Patent Number: 6,059,820
[45] Date of Patent: May 9, 2000

[54] TISSUE COOLING ROD FOR LASER SURGERY

[75] Inventor: Eugene Baronov, San Diego, Calif.

[73] Assignee: Paradigm Medical Corporation, Newport Beach, Calif.

[21] Appl. No.: 09/174,065

[22] Filed: Oct. 16, 1998

[51] Int. Cl.$^7$ .................................................. A61N 21/00
[52] U.S. Cl. .................................. 607/89; 606/9; 606/20
[58] Field of Search ..................................... 606/9, 10, 11, 606/12, 13, 14, 15, 16, 17, 20; 607/88, 89, 90

[56] References Cited

U.S. PATENT DOCUMENTS

| | | | |
|---|---|---|---|
| 4,376,376 | 3/1983 | Gregory | 606/22 |
| 5,334,016 | 8/1994 | Goldsmith et al. | 606/10 |
| 5,344,418 | 9/1994 | Ghaffari | 606/9 |
| 5,486,172 | 1/1996 | Chess | 606/20 |
| 5,735,844 | 4/1998 | Anderson et al. | 606/9 |
| 5,810,801 | 9/1998 | Anderson et al. | 606/9 |
| 5,814,040 | 9/1998 | Nelson et al. | 606/9 |
| 5,820,626 | 10/1998 | Baumgardner | 606/15 |
| 5,902,299 | 3/1999 | Jayaraman | 606/20 |

*Primary Examiner*—Linda C. M. Dvorak
*Assistant Examiner*—Soyu Han-Ogugua
*Attorney, Agent, or Firm*—John R. Ross; John R. Ross, III

[57] ABSTRACT

A laser treatment device and process with controlled cooling. The device contains a rod with high heat conduction properties, which is transparent to the laser beam. A surface of the rod is held in contact with the tissue being treated and other surfaces of the rod are cooled by the evaporation of a cryogenic fluid. The cooling is coordinated with the application of the laser beam so as to control the temperatures of all affected layers of tissues. In a preferred embodiment useful for removal of wrinkles and spider veins, the rod is a sapphire rod. A cryogenic spray cools the walls. A first surface is in contact with the skin surface being treated and an opposite surface is contained in an anticondensation oil chamber that is optically connected to a laser beam delivering fiber optic cable. In this preferred embodiment the temperature of the rod is monitored with a thermocouple which provides a feedback signal to a processor which controls the cooling and the laser power to provide proper regulation of temperatures at all affected tissue layers.

13 Claims, 7 Drawing Sheets

FIG. 3A
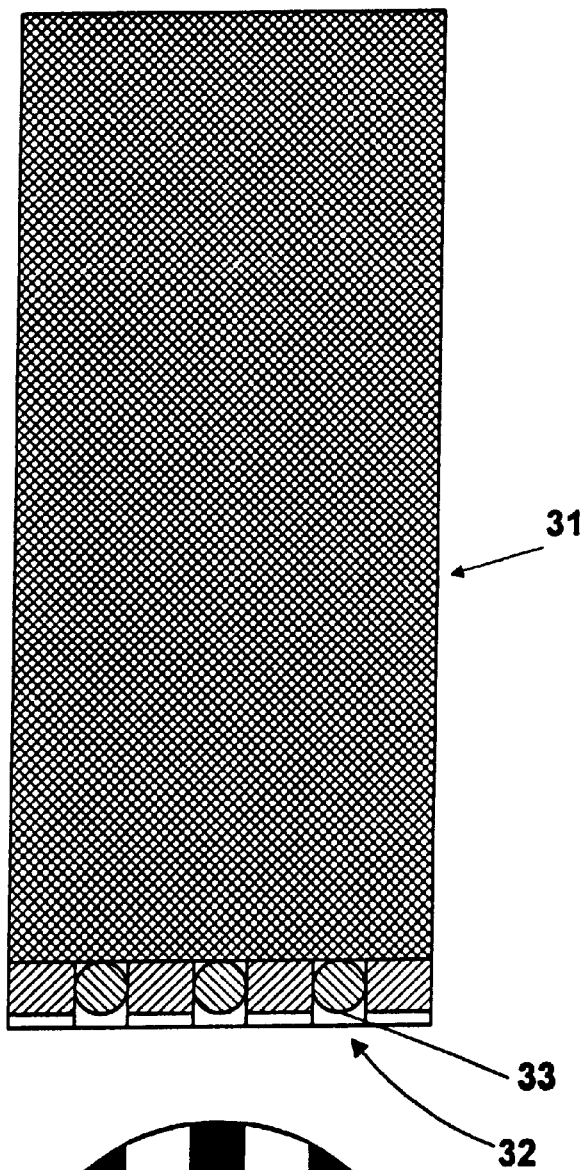
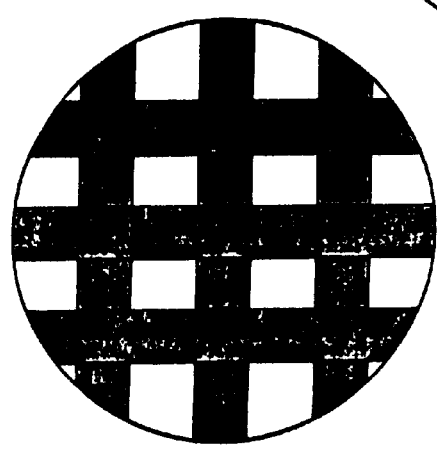
FIG. 3B

TISSUE COOLING ROD FOR LASER SURGERY

This invention relates to devices and methods for laser treatment and in particular to laser treatment with surface cooling.

BACKGROUND OF THE INVENTION

The principal methods presently used for skin cooling before or during the laser treatment involve the use of a cold contacting window or cryogenic spray device. Cryogenic spray directly to the skin may reduce a skin temperature below 0 C. but can freeze the skin and cause significant damage to it. Cold contacting windows of the prior art can cool the surface of the skin to as low as 4 C. But prior art cold contact window devices are inadequate to remove enough heat to prevent unwanted surface tissue damage in many applications.

Three prior art techniques are described in the following United States patents: C. Chess, Apparatus for treating cutaneous vascular lesions, U.S. Pat. No. 5,486,172; Anderson et al., U.S. Pat. No. 5,595,568; and C. Chess, Method for treating cutaneous vascular lesions, U.S. Pat. No. 5,282,797. All of these devices and methods provide for the cooling of the skin up to temperature of 4 C. but not below it.

A different technique is described by J. S. Nelson et al., in the article "Dynamic Epidermal Cooling in Conjunction With Laser-Induced Photothermolysis of Port Wine Stain Blood Vessels, Lasers in Surgery and Medicine 1996;19:224–229. In this technique the direct cryogenic spray to the skin surface is used before the laser pulse delivery. This method is normally not satisfactory. The surface gets too cold and the subsurface layers are not sufficiently cooled so that unwanted damage occurs at the surface because the tissue gets too cold from the cryogen and/or unwanted damage occurs in the immediate subsurface layers because the tissue gets too hot from the laser beam.

What is needed is a better laser surgery cooling method to better control tissue temperature during laser treatments.

SUMMARY OF THE INVENTION

The present invention provides a laser treatment device and process with controlled cooling. The device contains a rod with high heat conduction properties, which is transparent to the laser beam. A surface of the rod is held in contact with the tissue being treated and other surfaces of the rod are cooled by the evaporation of a cryogenic fluid.

The cooling is coordinated with the application of the laser beam so as to control the temperatures of all affected layers of tissues. In a preferred embodiment useful for removal of wrinkles and spider veins, the rod is a sapphire rod. A cryogenic spray cools the walls. A first surface is in contact with the skin surface being treated and an opposite surface is contained in an anticondensation oil chamber that is optically connected to a laser beam delivering fiber optic cable. In this preferred embodiment the temperature of the rod is monitored with a thermocouple which provides a feedback signal to a processor which controls the cooling and the laser power to provide proper regulation of temperatures at all affected tissue layers.

BRIEF DESCRIPTION OF THE DRAWINGS

FIGS. 3A and 3B show a partially masked cooling rod.

DETAILED DESCRIPTION OF PREFERRED EMBODIMENTS

Preferred embodiments of the present invention can be described by reference to the figures.

COOLING AND SUBSURFACE LIGHT DELIVERY METHOD

Skin Surface Cooling

Figure 1:
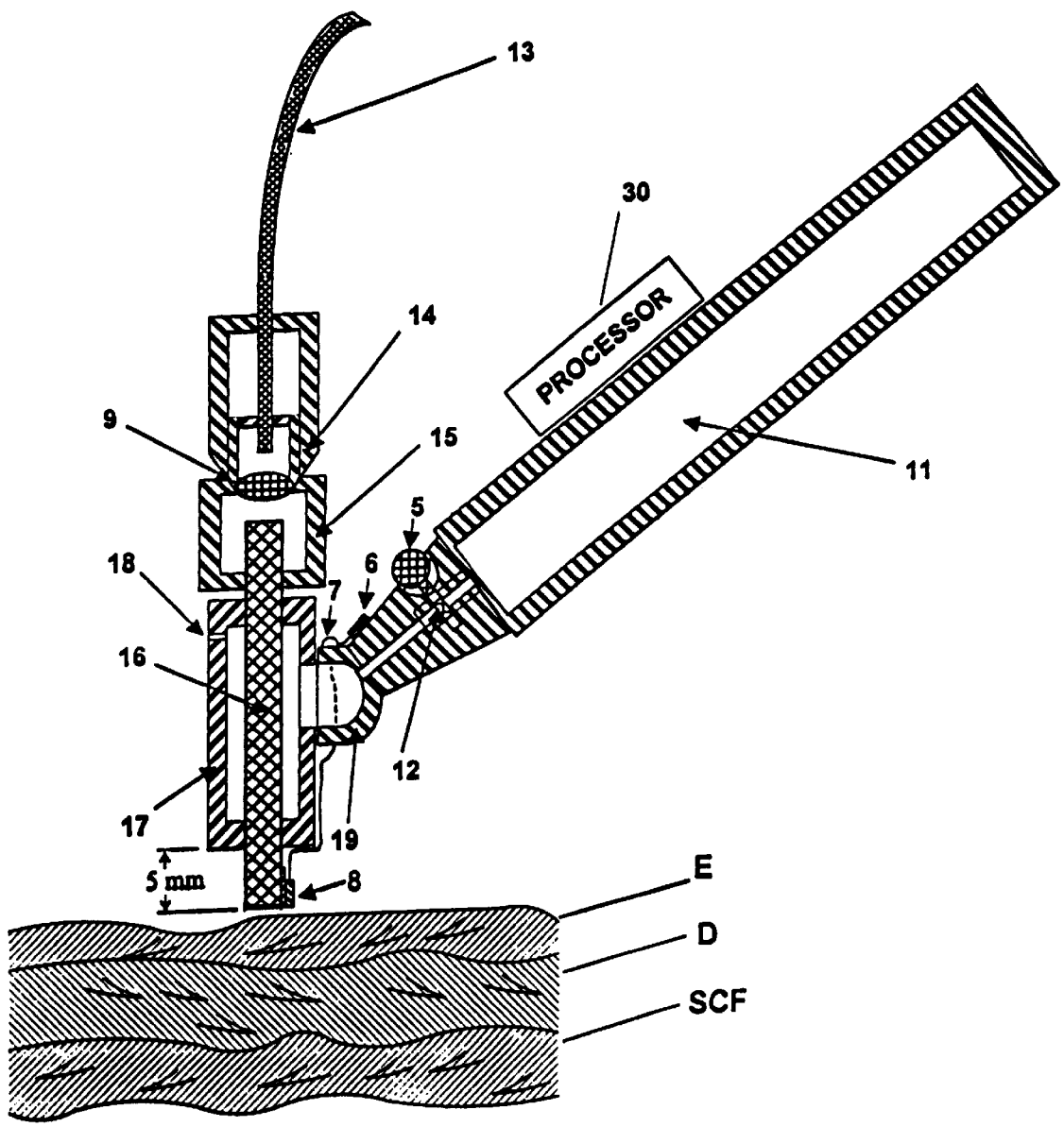
FIG. 1 is a drawing of the cooling rod hand piece for the subsurface light energy delivery.

A section of human skin with a cooling cryogenic rod device in accordance with the present invention is shown in FIG. 1. FIG. 1 shows a cryogenic container 11 that also serves as a handle for the device. A nozzle 19 with a valve 12 and a valve-opening actuator 5 provides for a cryogenic spray onto the portion of sapphire rod 16 within cryogenic cooling chamber 17. In this embodiment the cryogen is Tetrafluoethan. The cryogenic mist exhausts through port 18. An anti condensation oil chamber 15 contains collimating lens 9, a fiber holder 14 optically connecting delivery fiber optic cable 13 and a transparent optical oil, which in this embodiment is microscopic immersion oil. In this embodiment the laser beam is provided by an Er:Glass pulse laser producing 25 Joule 2 ms pulses at pulse rates of 1 Hz or 0.5 Hz. A thermocouple 8 is insulated from rod 16 and senses the temperature of the skin surface and provides a feedback signal to processor 30 which controls delivery of the cryogen spray via actuator 5 and the laser pulses through the laser controls (not shown). Also shown on FIG. 1 is "ready" light 7 and battery 6 which powers the light and the thermocouple. FIG. 1 also shows a section of human skin including epidermis E, dermis D and a subcutaneous fat SCF.

The section of skin is first cleaned with alcohol to remove moisture to prevent a condensation on the contacting surface of the rod and in order to dehydrate the skin surface to reduce the epidermal damage from the light interaction with water. When the valve of the nozzle is opened the cryogen coolant is sprayed micro drops into the cooling chamber. The cryogenic mist flows around the sapphire. The micro drops contact the rod and vaporize from the surface of the rod by the rod heat reducing the rod temperature dramatically fast. The whole rod becomes cold almost instantly because of the high thermoconductivity of sapphire. The sapphire rod cools the surface of the skin by heat exchange.

Treatment for Spider Veins

Figure 2:
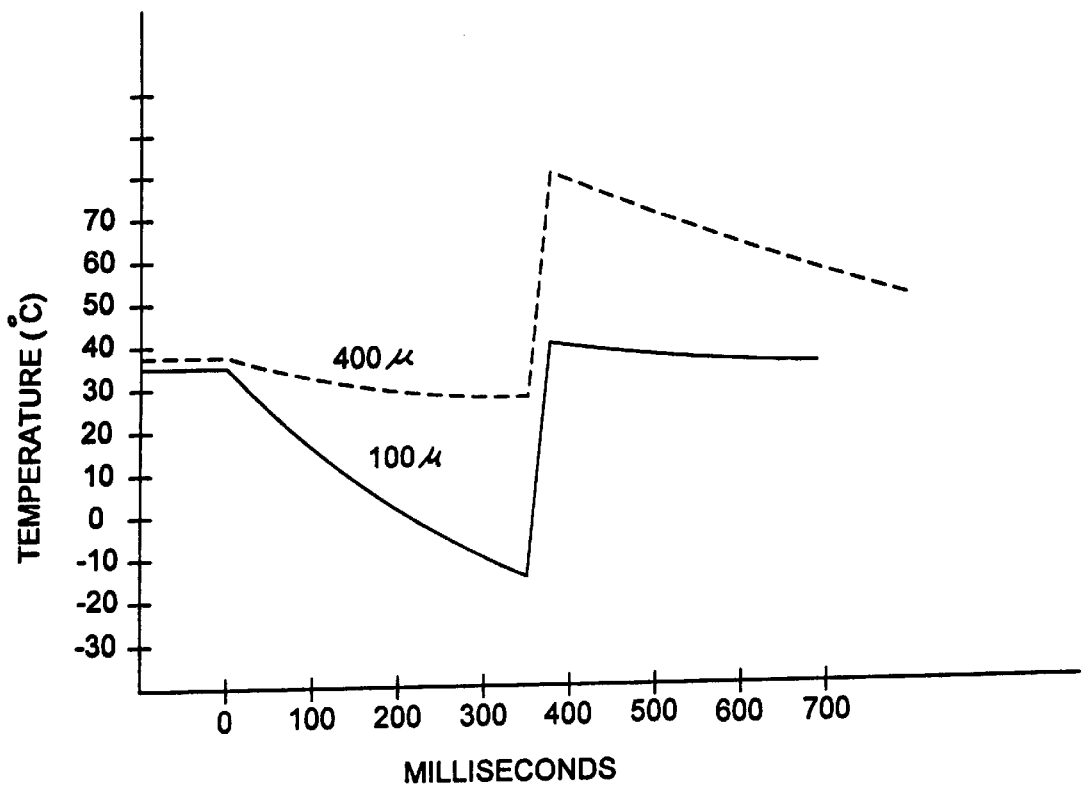
FIGS. 2 is a time graph showing temperature changes below the skin surface.

A preferred application of the device shown in FIG. 1 is for spider vein removal. The operator presses the tip of the device against the skin as shown in FIG. 1 and presses the on button. The processor opens valve 12 permitting cryogen flow. The processor 30 monitors the skin temperature via thermocouple 8 and assures that the skin temperature is not below 0 C. for more than 1 second. When processor 30 determines that the temperature of the surface has dropped to a desired low temperature at a desired rate, such as −15 C. in a time period of 0.30 to 0.40 seconds, the "lasing" light indicator is switched-on and the processor will direct the laser to fire a pulse. Each pulse will heat the skin by about 50 C. Thus, tissue cooled to −15 C. will after the laser pulse be at a temperature of about 35 C. which is close to normal skin temperature. Blood in spider veins just below the epidermis which prior to the laser pulse is at a temperature of about 25 C. will be heated to slightly over 70 C. to destroy the vein tissue. FIG. 2 shows graphs of the temperature of the skin at points 100 microns below the skin surface (near the bottom boundary of the epidermis) and 400 microns below the surface of the skin (at the center of a 200 micron diameter spider vein) during the above described process. The reader should note that the tissue at a depth of 100 microns is below 0 C. for about 100 milliseconds and that the tissue at 400 microns is above 70 C. for about 100 milliseconds. It is well known that tissue is not adversely affected by subfreezing temperatures in this range until the time periods are more than about 500 ms. On the other hand, however temperatures in excess of 70 degrees for about 10 ms will coagulate the tissue.

Figure 7A:
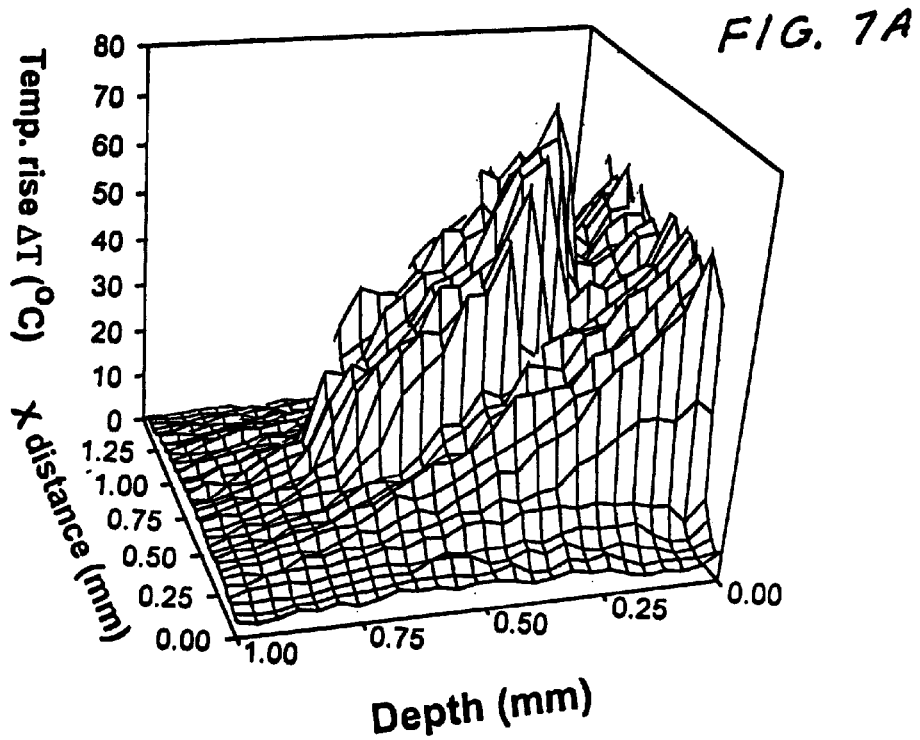
FIGS. 7A and 7B are temperature profile charts.
Figure 7B:
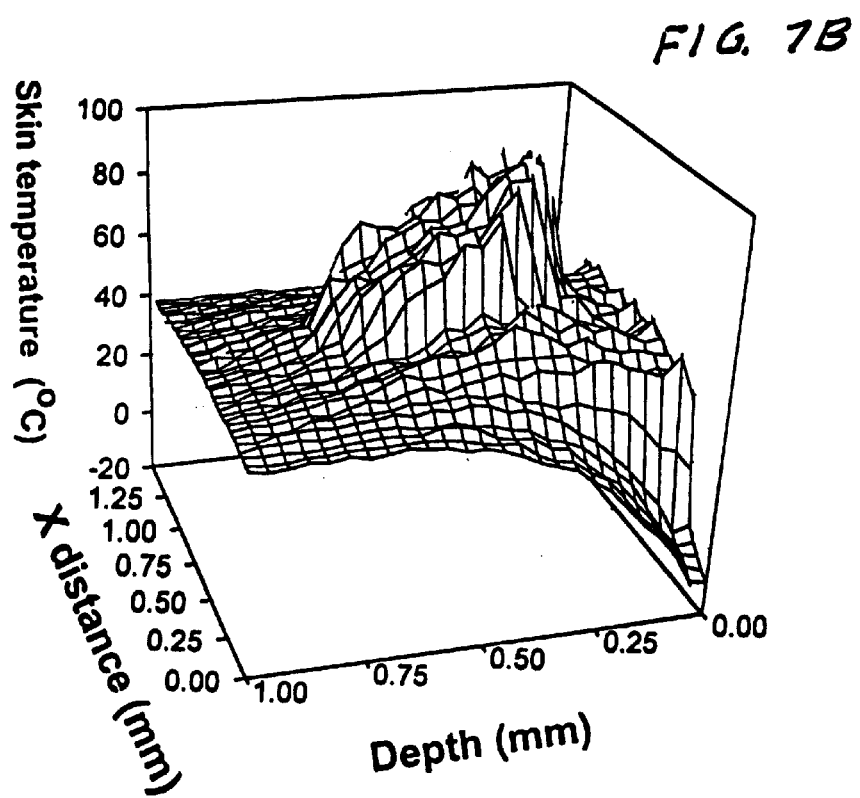

The processor will stop the lasing if thermocouple 8 indicates an excessive temperature which in this procedure would be about 60 C. The thermocouple 8 is preferably calibrated to the temperature of the skin located in one millimeter from the rod edge. The difference between the temperature of the skin under the rod and in 1 mm from the rod edge is varied from 10 C. to 20 C. and depending upon the rod design. Applicant has performed computer simulations to determine temperature profiles in the case of laser treatments with and without surface cooling. FIG. 7A shows the effects of a 20 J/cm$^2$,1540-mm diameter blood vessel, and 0.5 mm below the skin surface, with no surface cooling. FIG. 7B represents a similar conditions with surface cooling with a −15° C. sapphire glass rod for 0.5 sec.

Mechanical contact, optical, electrical or other sensor can be used to trigger the time delay circuit after the cold rod touches the skin for the definite time. The time delay is defined by the procedure and by the anatomical structure of the skin and blood vessel.

Treatment for Wrinkles

It is known that an effective treatment for the removal of wrinkles is to destroy a line of tissue just below the epidermis at the bottom of the wrinkle valley. Scar tissue forms in the place of the destroyed tissue pushing up the bottom of the valley and effectively removing the wrinkle. The problem is how do you destroy the tissue below the epidermis without also destroying the epidermis and thus replacing an ugly wrinkle with an ugly scar. The present invention provides the solution. Using substantially the same procedure as described above, the tissue at the bottom of the wrinkle valley is destroyed without any significant damage to the epidermis. Details and parameters are outlined below.

Laser Application

The laser device used in this preferred embodiment is a free running mode Er:Glass pulse laser which has the spike in the range of 1.54 microns. Light in this range has minimal scattering losses in the skin and is readily absorbed in the skin water. Laser parameters such as pulse width, energy density, repetition rate can be selected to best fit the skin and the treated lesion of the patients. The parameters for two specific examples which have been utilized with good results for wrinkle removal and leg vein treatment are shown in Table 1:

TABLE 1

Parameters Preferred

|  | Wrinkles | Spider Veins |
|---|---|---|
| Pulse Width | 2 ms | 2 ms |
| Repetition Rate | 1 Hz | 0.5 Hz |
| Sapphire Rod Diameter | 3 mm | 2 mm |
| Spot Size | 7.2 mm$^2$ | 3.14 mm$^2$ |
| Energy Density | 25 J/cm$^2$ | 25 J/cm$^2$ |

Each point on the skin receives a high energy density illumination for about 2 milliseconds. Some of the light is reflected. Of the light which is not reflected a significant portion of the energy of each pulse penetrates to the depth up to 1–1.5 mm and is absorbed by the skin water.

Operating within the parameters specified is important. They have been chosen to preferentially cool the skin surface protecting epidermis and to heat the subepidermal collagen or blood vessels to the level of irreversible changes in the coagulated skin tissue and blood vessel proteins. It must be chosen so that a large amount of energy is deposited in the skin quickly so that the temperature of the targeted tissue rises rapidly to about or slightly above 70° C. The cooling applied to the surface for about half a second is enough to protect epidermis from the temperature increasing to 70° C. Thus the above procedure can be used effectively for treatment spider veins.

Estimation of Temperature Rise in Human Skin

Estimation of temperature rise in skin can be made by calculating laser light fluence in skin and estimating energy deposition per unit volume of skin. Effect of contact skin surface cooling was accounted based on solution of heat transfer equation.

In order to estimate light fluence in skin the following optical properties of tissue have been used:

|  | Absorption coef (1/cm) | Scattering coef (1/cm) | Asymmetry Factor (g) | Refr. Index n | Thickness |
|---|---|---|---|---|---|
| Epidermis | 5 | 300 | 0.8 | 1.4 | 100 micron |
| Dermis | 5 | 100 | 0.85 | 1.4 | Semiinfinite |
| Blood | 10 | 300 | 0.98 | 1.4 | N/A |

At 1.54 micron absorption in tissues is determined by their water content. Water content of whole blood is more then 90%, whereas in dermis and epidermis it is about twice less. For this reason absorption of IR radiation and temperature rise in blood is expected to be about two times higher than in surrounding dermis tissue. Once fluence in the skin is calculated the temperature rise $\Delta T$ due to light absorption can be estimated as follows:

$$\Delta T = abs.coef * Fluence/(density * Spec.heat.of\ skin)$$

where skin density is about 1.1–1.2 g/cm$^3$ and specific heat of skin about 3.5–4 Jouls*° C./(g*cm$^3$).

Effect of skin surface cooling on temperature distribution in skin have been estimated by solving heat transfer equation in semi infinite skin tissue with boundary conditions corresponding to constant −5° C. temperature of the surface (or other constant temperature of the sapphire rod). Temperature distribution in °C. in skin then can be calculated by formula:

$$T(z, t) = 37 * erf\left(\frac{z}{2\sqrt{\alpha t}}\right)$$

Where z is the depth into the tissue, t is time lapse in seconds from the start of the contact skin cooling and $\alpha=10^{-4}$(cm$^2$/sec) is thermal diffusivity of skin dermis. Skin temperature was found by superposition of laser heating and surface cooling effects.

Cooling experiments have been performed by using different configurations of the cold rod for the different applications. For these applications, one of the alternative embodiments is recommended.

CRYOGENICALLY COOLED SELF CONTAINED WINDOW

A second embodiment involves the use of a cryogenically cooled diamond rod as shown in FIGS. 2A and 2B. The device consists of copper holder 24, which has a cryogenic container 21. Synthetic diamond rod 23 is in the shape of a flattened cylinder and contains a circular groove through which cryogenic mist flows. The mist exits at the exit port 26.

The flattened diamond rod is transparent to the laser beam. It is applied to the part of the cleaned skin to be treated. The nozzle valve opens the shutter and the cryogenic spray flows to the chamber around this window. When the window is cold the "ready" light will be switched-on. The energy delivery procedure can be started. This device is good for the large area irradiation such as subsurface tumor interstitial thermotherapy with a high frequency electromagnetic radiation.

PATERNED ROD FOR MASKING PORTIONS OF TISSUE

A third embodiment for practicing this invention is to use a patterned rod to the surface of the skin in order to have damaged and healthy areas under the skin surface. FIGS. 3A and 3B show rod 31 with the perpendicular grooves 32 filled with copper stripes 33.

A laser light is sent through the cooled rod to the surface of the skin does not penetrate through the copper stripes. But the contacting surface of the rod has an almost uniform temperature distribution. It means that the surface of the skin is cooled uniformly. But under skin damage is not uniform having irradiated and not irradiated healthy spots. The reason to have these healthy untouched spots around the damaged tissue is to use the capacity of healthy spot tissue and cells for the fast immune response and wound healing process.

SELF COLLIMATED COOLING ROD

Figure 4:
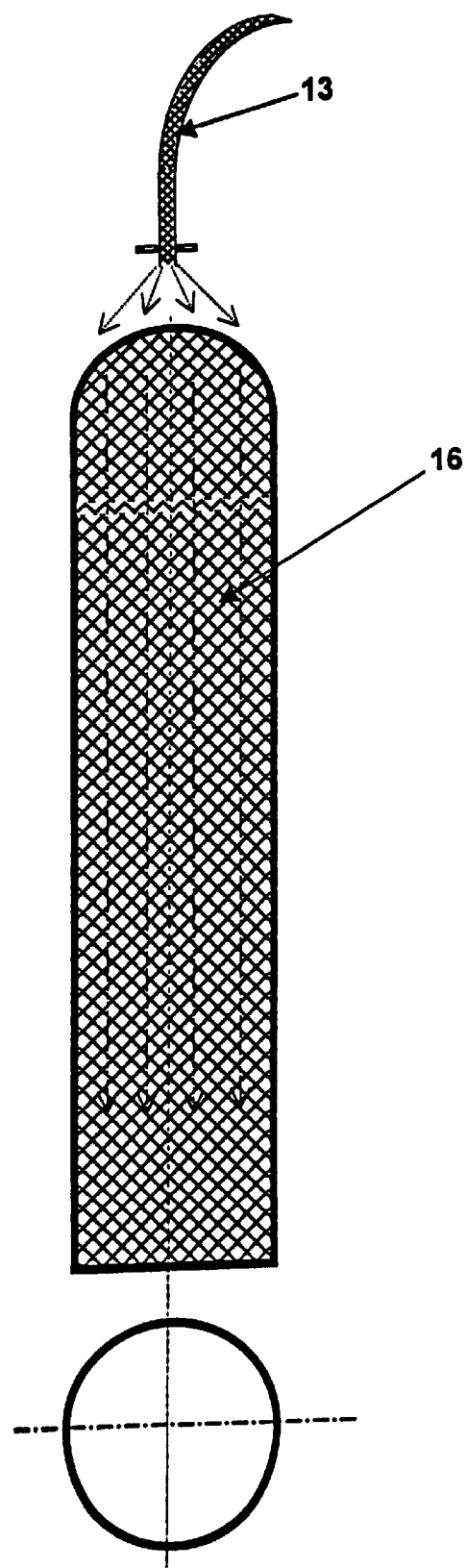
FIG. 4 shows a rod with the lens-type tip surface.
Figure 5A:
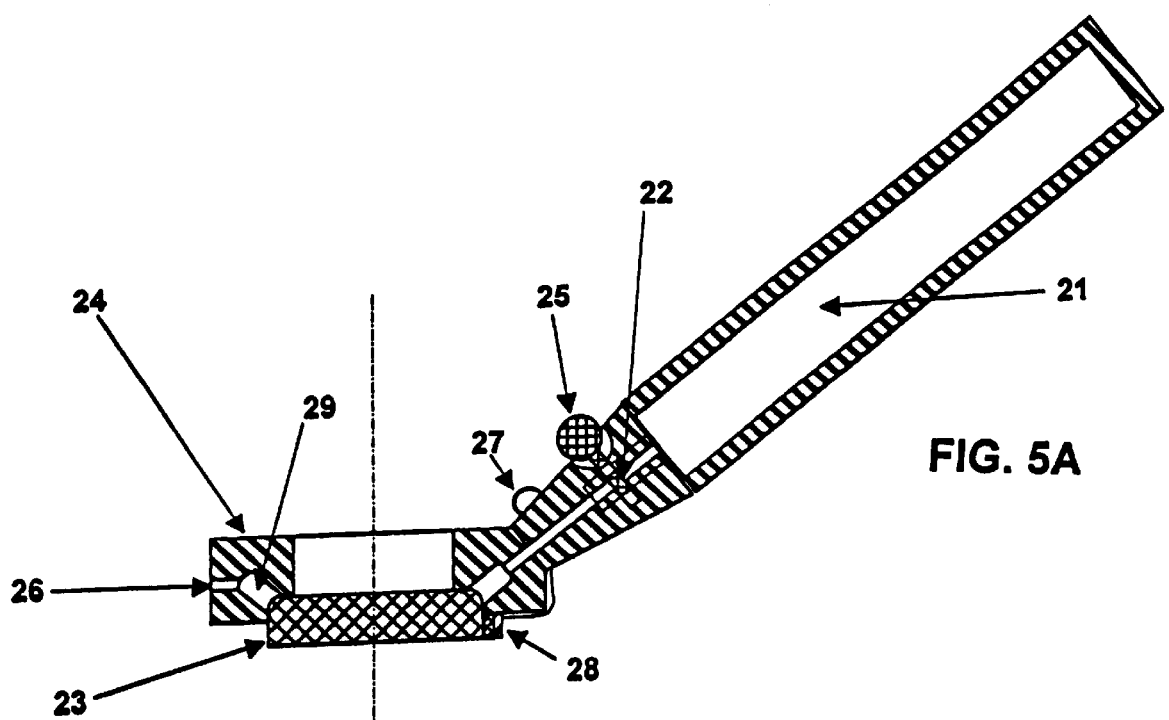
FIGS. 5A and 5B is a second preferred embodiment.
Figure 5B:
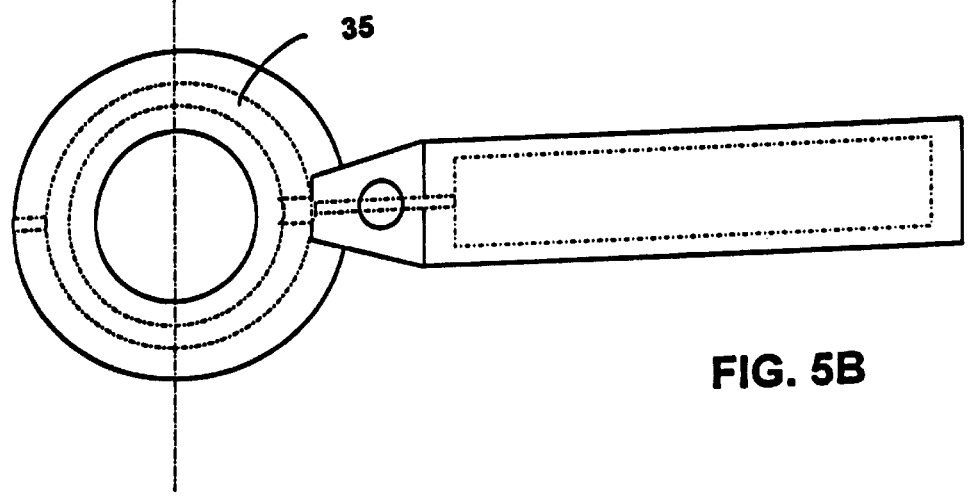

This embodiment is essentially the same as the first one described above except that the rod tip, which is connected to the fiber optics has concave form for the self-collimating beam properties. FIG. 4 shows a rod with the lens-type tip surface. For such a rod, it does not require a collimated lens and can be replaced by the transparent disk-type window in the oil chamber.

HORIZONTAL AND ANACHROMATIC COOLING ROD

Figure 6A:
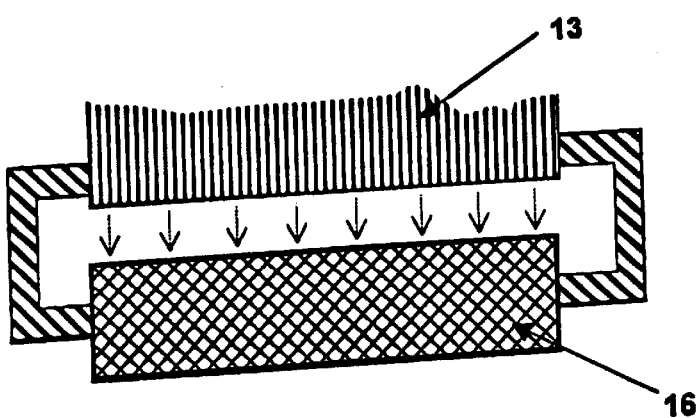
FIG. 6 shows a drawing of the horizontally positioned cooling rod.
Figure 6B:
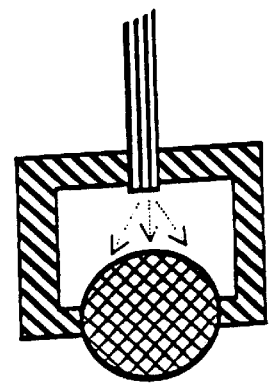

This embodiment is essentially the same as the first one described above except that the cylindrical rod is placed in the cooling chamber horizontally (see FIGS. 6A and 6B). The reader should note that the rod could be of different shapes to provide desired beam profiles on the skin surface or to focus the beam. The focal point (or focal line) could be under the skin to help concentrate the beam energy in target locations.

OTHER EMBODIMENTS

It is very important for all of these embodiments and in other embodiments that will be apparent to persons skilled in the art that the cooling rod has a very high thermoconductivity coefficient and low absorption of the irradiating light. The substance used for the cryogenic cooling can be chosen based on the particular application. The important thing is to use a proper time of cooling in order to reach a required low temperature of the tissue at the required depth. Persons skilled in the art will recognize that certain material and configuration of the rod, container, coolant and connector will be preferred for different skin type, different lesions and different applications. The reader should note that the preferred embodiment of this invention can be used without this laser to provide cryogenic treatment to surface skin lesions. The same skin cooling can be provided with about $\frac{1}{10}$ the cryogen as direct open spray.

While the above description contains many specifications, the reader should not construe these as limitations on the scope of the invention, buy merely as exemplifications of preferred embodiments thereof. Those skilled in the art will envision many other possible variations are within its scope. Accordingly the reader is requested to determine the scope of the invention by the appended claims and their legal equivalents, and not by the examples which have been given.

I claim:

1. A laser device for tissue treatment, comprising:
    A) a source of laser light defining a nominal wavelength,
    B) a cooling transmitting rod comprised of a material transparent to light at said nominal wavelength and having high thermal conductivity and having a contact surface for contacting a surface of tissue being treated,
    C) a cryogenic container,
    D) a cryogen contained in said container,
    E) a cryogenic cooling chamber for cooling said rod, said rod having a surface area in communication with said cooling chamber and said chamber having an entrance port communicating with said container and an exit port,
    F) a cryogenic control means for permitting a flow of vaporizing cryogen from said container into said chamber to cool said rod in order to remove heat from said tissue surface and to produce desired temperature distribution in target tissue during a laser treatment of said tissue.

2. A laser device as in claim 1 and further comprising a temperature-monitoring element mounted adjacent to but insulated from said contact surface for monitoring tissue surface temperature.

3. A laser device as in claim 1 and further comprising a processor programmed for controlling said source of laser light and said flow of cryogen.

4. A laser device as in claim 1 wherein said source of laser light is a free running mode Er:Glass pulse laser.

5. A laser device as in claim 1 wherein said cooling transmitting rod is sapphire rod.

6. A laser device as in claim 1 wherein said cooling transmitting rod is a diamond rod.

7. A laser device as in claim 1 wherein said cooling transmitting rod is a patterned rod.

8. A laser device as in claim 1 wherein said cooling transmitting rod has a distal end with a concave surface for collimating the beam.

9. A process for treating tissue, comprising the steps of:
   A) generating from a source of laser light defining a nominal wavelength,
   B) transmitting said laser light through a cooling transmitting rod comprised of material transparent to light at said nominal wavelength and having high thermal conductivity and having a contact surface for contacting a surface of tissue being treated said rod having a surface area in communication with said cooling chamber and,
   C) inserting cryogen from a cryogenic container into a cryogenic cooling chamber for said rod, said chamber having an entrance port communicating with said container and an exit port, wherein said inserting permits a flow of vaporizing cryogen from said container into said chamber to cool said rod in order to remove heat from the tissue surface and to produce desired temperature distribution in target tissue.

10. A process as in claim 9, further comprising the step of:
    A) monitoring tissue surface temperature with a temperature monitoring element mounted adjacent to but insulated from said contact surface.

11. A process as in claim 9, further comprising the step of:
    A) controlling said source of laser light and said flow of cryogen with a processor programmed with a control algorithm.

12. A process as in claim 9, wherein said method is for the purpose of treating spider veins.

13. A process as in claim 9, wherein said method is for the purpose of treating wrinkles.

\* \* \* \* \*